(12) United States Patent
Boehringer et al.

(10) Patent No.: US 7,411,093 B2
(45) Date of Patent: Aug. 12, 2008

(54) AMINOCYCLOALKANES AS DPP-IV INHIBITORS

(75) Inventors: Markus Boehringer, Moehlin (CH); Daniel Hunziker, Moehlin (CH); Bernd Kuhn, Liestal (CH); Bernd Michael Loeffler, Zug (CH); Hans Peter Marty, Basel (CH); Patrizio Mattei, Riehen (CH); Robert Narquizian, St. Louis (FR)

(73) Assignee: Hoffman-La Roche Inc., Nutley, NJ (US)

( * ) Notice: Subject to any disclaimer, the term of this patent is extended or adjusted under 35 U.S.C. 154(b) by 62 days.

(21) Appl. No.: 11/302,067

(22) Filed: Dec. 13, 2005

(65) Prior Publication Data

US 2006/0135512 A1  Jun. 22, 2006

(30) Foreign Application Priority Data

Dec. 20, 2004  (EP) .................................. 04106704

(51) Int. Cl.
*C07C 211/35* (2006.01)
*C07D 207/323* (2006.01)
*C07D 333/02* (2006.01)
*C07D 333/08* (2006.01)
*C07D 211/40* (2006.01)
*C07D 211/54* (2006.01)
*C07D 279/02* (2006.01)
*A61K 31/135* (2006.01)
*A61K 31/40* (2006.01)
*A61K 31/38* (2006.01)
*A61K 31/445* (2006.01)
*A61K 31/54* (2006.01)

(52) U.S. Cl. .................... 564/307; 548/564; 549/29; 549/83; 546/216; 544/3; 514/222.2; 514/327; 514/427; 514/438; 514/647

(58) Field of Classification Search ........................ None
See application file for complete search history.

(56) References Cited

U.S. PATENT DOCUMENTS

| | | | |
|---|---|---|---|
| 6,011,155 | A | 1/2000 | Villhauer |
| 6,110,949 | A | 8/2000 | Villhauer |
| 6,303,661 | B1 | 10/2001 | Demuth et al. |
| 6,319,893 | B1 | 11/2001 | Demuth et al. |
| 6,476,025 | B1 | 11/2002 | Gutterer |
| 2002/0071838 | A1 | 6/2002 | Demuth et al. |
| 2005/0107309 | A1 | 5/2005 | Demuth et al. |

FOREIGN PATENT DOCUMENTS

| | | |
|---|---|---|
| DE | 2133473 A1 | 1/1973 |
| DE | 19616486 | 10/1997 |
| DE | 19834591 | 2/2000 |
| WO | WO 91/11437 A1 | 8/1991 |
| WO | WO 97/28131 A1 | 8/1997 |
| WO | WO98/19998 | 5/1998 |
| WO | WO 99/38501 | 8/1999 |
| WO | WO 00/34241 | 6/2000 |
| WO | WO 01/40180 | 6/2001 |
| WO | WO 01/42203 A1 | 6/2001 |
| WO | WO 01/55105 | 8/2001 |

OTHER PUBLICATIONS

The American Heritage Dictionary of the English Language 4th ed. (2000), Houghton Mifflin Co., Boston, NY, p. 1406.*
Shepherd, T.A., et al., Journal of Medicinal Chemistry, 45(10), p. 2101-2111 (2002), XP002373142.
Lowry, B.R., et al., J. Pharm Sci., vol. 60, No. 4, pp. 632-633, (1971), XP002218826.
Ganesh Pandey, et al., Tetrahedron Letters, vol. 31, No. 37, pp. 5373-5376 (1990), XP002373144.
M.F.F.;, Rahman, J. Heterocyclic Chem., vol. 13, pp. 1329-1331 (1976), XP002373145.
F. Vlaeminck, et al., Benzo-And Indoloquinolizidines, Part XVIII, vol. 12, No. 3, pp. 329-335 (1979).
Govindachari, et al., J. Chem. Soc., pp. 4280-4283 (1956), XP000571477.
C.M. Nachtsheim, et al., Arch. Pharm., vol. 322, pp. 199-206 (1989), XP009063594.
Hosano O. et al., Modern Rheumatology 2003, 13(3), 199-204.
Boonacker E.; Van Noorden C. J. F, European Journal of Cell Biology 2003, 82(2), 53-73.
Aytac U., Dang, N. H., Current Drug Targets: Immune, Endocrine and Metabolic Disorders 2004, 4(1), 11-18.

* cited by examiner

*Primary Examiner*—Brian Davis
(74) *Attorney, Agent, or Firm*—George W. Johnston; Dennis P. Tramaloni; Samuel H. Megerditchian

(57) ABSTRACT

The present invention relates to compounds of formula (I)

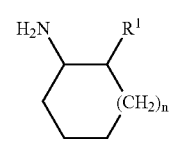

wherein $R^1$ is as defined in the description and claims, and pharmaceutically acceptable salts thereof. The compounds are useful for the treatment and/or prophylaxis of diseases which are associated with DPP-IV, such as diabetes, particularly non-insulin dependent diabetes mellitus, and impaired glucose tolerance.

11 Claims, No Drawings

AMINOCYCLOALKANES AS DPP-IV INHIBITORS

PRIORITY TO RELATED APPLICATIONS

This application claims the benefit of European Application No. 04106704.2, filed Dec. 20, 2004, which is hereby incorporated by reference in its entirety.

FIELD OF THE INVENTION

The present invention is directed to, for example, novel cycloalkylamine derivatives, their manufacture and their use as medicaments.

In particular, the invention involves, for example, compounds of the formula (I)

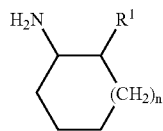

I and pharmaceutically acceptable salts thereof for use in therapy.

All documents cited or relied upon below are expressly incorporated herein by reference.

BACKGROUND OF THE INVENTION

The enzyme dipeptidyl peptidase IV (EC.3.4.14.5, abbreviated in the following as DPP-IV) is involved in the regulation of the activities of several hormones. In particular DPP-IV is degrading efficiently and rapidly glucagon like peptide 1 (GLP-1), which is one of the most potent stimulator of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycaemia and accordingly reduce the risk of tissue damage. Consequently, DPP-IV inhibitors have been suggested as drug candidates for the treatment of impaired glucose tolerance and type 2 diabetes mellitus (e.g. Villhauer, WO98/19998). Other related state of the art can be found in WO 99/38501, DE 19616486, DE 19834591, WO 01/40180, WO 01/55105, U.S. Pat. No. 6,110,949, WO 00/34241 and U.S. Pat. No. 6,011,155.

Furthermore, DPP IV contributes to the generation and modulation of a T cell immune response. DPP IV (also known as CD26) has an essential role in immune regulation as a T cell activation molecule and a regulator of chemokine function thus suggesting a role for DPP-IV in the pathophysiology of immune-mediated disorders as well as autoimmune diseases (Hosano O. et al., Modern Rheumatology 2003, 13(3), 199-204). Abnormal expression of DPP-IV is found in the case of autoimmune diseases, HIV-related diseases and cancer. Natural substrates for DPP-IV are involved in immunomodulation, psycho/neuronal modulation and physiological processes in general (Boonacker E.; Van Noorden C. J. F, European Journal of Cell Biology 2003, 82(2), 53-73). Furthermore, it has been shown that there is a correlation between DPP-IV and the key nuclear protein topoisomerase alpha (Aytac U., Dang, N. H., Current Drug Targets: Immune, Endocrine and Metabolic Disorders 2004, 4(1), 11-18). Thus, DPP-IV inhibitors may be useful as medicaments for the treatment of various diseases in which DPP-IV is involved.

SUMMARY OF THE INVENTION

In one embodiment of the present invention, provided is a compound of the formula (I):

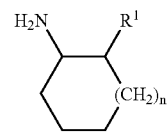

I wherein:

$R^1$ is selected from

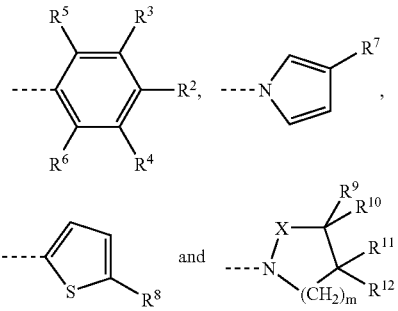

$R^2$, $R^3$, $R^4$, $R^5$ and $R^6$ are each independently selected from hydrogen, lower alkyl, halogenated lower alkyl, lower alkoxy or halogen; provided that $R^2$, $R^3$, $R^4$, $R^5$ and $R^6$ are not all hydrogen;

$R^7$ is lower alkyl;

$R^8$ is lower alkyl;

X is >C=O or >SO$_2$;

$R^9$ and $R^{11}$ are hydrogen or together form a double bond;

$R^{10}$ and $R^{12}$ are independently selected from hydrogen or lower alkyl;

m is 1 or 2;

n is 0, 1, or 2;

and pharmaceutically acceptable salts thereof for the use in therapy.

In another embodiment of the present invention, provided is a compound according to formula (I):

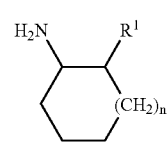

I wherein:

$R^1$ is selected from

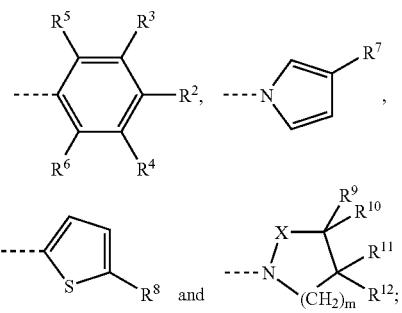

$R^2$, $R^3$, $R^4$, $R^5$ and $R^6$ are each independently selected from hydrogen, lower alkyl, halogenated lower alkyl or halogen; provided that $R^2$, $R^3$, $R^4$, $R^5$ and $R^6$ are not all hydrogen;
$R^7$ is lower alkyl;
$R^8$ is lower alkyl;
X is >C=O or >SO$_2$;
$R^9$ and $R^{11}$ are hydrogen or together form a double bond;
$R^{10}$ and $R^{12}$ are independently selected from hydrogen or lower alkyl;
m is 1 or 2;
n is 0, 1, or 2;
and pharmaceutically acceptable salts thereof,
with the further proviso that the following compounds are excluded
2-(m-tolyl)-cyclohexylamine, 2-(p-tolyl)-cyclohexylamine, 2-(o-tolyl)-cyclohexylamine, 2-(2-chlorophenyl)-cyclohexylamine, 2-(3-chlorophenyl)-cyclohexylamine, 2-(p-chlorophenyl)-cydohexylamine, 2-(2-bromophenyl)-cyclohexylamine, 2-(o-tolyl)-cyclopentylamine, 2-(p-tolyl)-cyclopentylamine,
2-(4-chlorophenyl)-cyclopentylamine, 2-(3,5-difluorophenyl)-cyclopentylamine, 2-(3-fluorophenyl)-cyclpentylamine, 2-(4-fluorophenyl)-cyclopentylamine,
2-(4-bromophenyl)-cyclopentylamine, and
2-(4-tert-butylphenyl)-cyclopentylamine.

In a further embodiment of the present invention, provided is a process for manufacturing a compound according to formula I, comprising the steps of: a reductive amination of a ketone of formula II

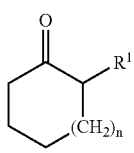

II wherein $R^1$ and n are as defined above, or a deprotection of a carbamic acid ester of formula III

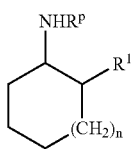

III wherein $R^1$ and n are as defined above and $R^P$ is an amino protecting group.

In a yet another embodiment of the present invention, provided is a pharmaceutical composition, comprising a therapeutically effective amount of a compound of formula I

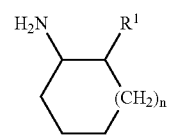

I wherein
$R^1$ is selected from

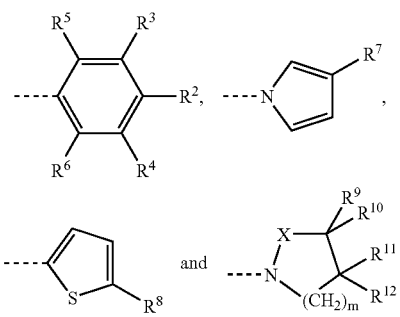

$R^2$, $R^3$, $R^4$, $R^5$ and $R^6$ are each independently selected from hydrogen, lower alkyl, halogenated lower alkyl, lower alkoxy or halogen; provided that $R^2$, $R^3$, $R^4$, $R^5$ and $R^6$ are not all hydrogen;
$R^7$ is lower alkyl;
$R^8$ is lower alkyl;
X is >C=O or >SO$_2$;
$R^9$ and $R^{11}$ are hydrogen or together form a double bond;
$R^{10}$ and $R^{12}$ are independently selected from hydrogen or lower alkyl;
m is 1 or 2; and
n is 0, 1, or 2;
or a pharmaceutically acceptable salt thereof;
and a pharmaceutically acceptable carrier and/or adjuvant.

In a still further embodiment of the present invention, provided is a pharmaceutical composition, comprising a therapeutically effective amount of a compound according to formula I and a pharmaceutically acceptable carrier and/or adjuvant.

In a yet still another embodiment of the present invention, provided is a method for the treatment and/or prophylaxis of diseases which are associated with DPP-IV, comprising the step of administering a compound according to formula I to a human being or animal in need thereof.

DETAILED DESCRIPTION

Provided herein are novel DPP-IV inhibitors that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. In addition, the compounds of the present invention can also be used in the treatment and/or prophylaxis of obesity, metabolic syndrome, β-cell protection, autoimmune diseases such as inflammatory bowel disease, encephalitis periaxialis scleroticans and rheumatoid arthritis, Colitis Ulcerosa, Morbus Crohn, psoriasis, lichen planus and/or benign prostate hypertrophy. The compounds may also be useful for the prevention of AIDS (acquired immunodeficiency syndrome) or for preventing metastasis, particularly preventing metastasis of breast and prostate cancer to lung. Furthermore, the compounds of the present invention can be used as diuretic agents and for the treatment and/or prophylaxis of hypertension.

The compounds of the present invention exhibit improved therapeutic and pharmacological properties compared to other DPP-IV inhibitors known in the art, such as e.g. in context of pharmacokinetics and bioavailability.

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine, bromine and chlorine being preferred. Most preferred halogen is chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "halogenated lower alkyl" refers to a lower alkyl group wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with fluoromethyl being especially preferred.

The term "alkoxy" refers to the group R'—O—, wherein R' is alkyl. The term "lower-alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment, the present invention relates to compounds for use in therapy having the formula (I)

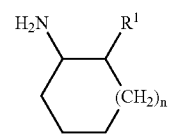

wherein
R$^1$ is selected from

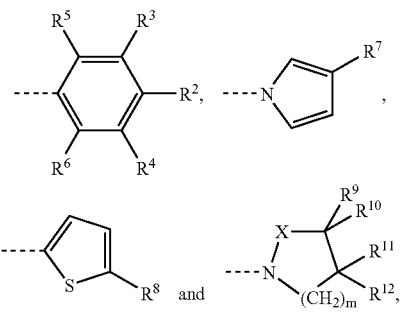

R$^2$, R$^3$, R$^4$, R$^5$ and R$^6$ are each independently selected from hydrogen, lower alkyl, halogenated lower alkyl, lower alkoxy or halogen; provided that R$^2$, R$^3$, R$^4$, R$^5$ and R$^6$ are not all hydrogen;
R$^7$ is lower alkyl;
R$^8$ is lower alkyl;
X is >C=O or >SO$_2$;
R$^9$ and R$^{11}$ are hydrogen or together form a double bond;
R$^{10}$ and R$^{12}$ are independently selected from hydrogen or lower alkyl;
m is 1 or 2;
n is 0, 1, or 2;
and pharmaceutically acceptable salts thereof.

In one further embodiment, the invention relates to compounds of formula (I) for use in therapy, wherein R$^1$ is

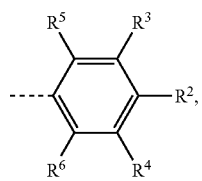

wherein R$^2$, R$^3$, R$^4$, R$^5$ and R$^6$ are each independently selected from hydrogen, lower alkyl halogenated lower alkyl, lower alkoxy or halogen; provided that R$^2$, R$^3$, R$^4$, R$^5$ and R$^6$ are not all hydrogen.
R$^2$ preferably has the meaning of hydrogen, lower alkyl or halogen, more preferably of hydrogen, methyl or chlorine.
R$^3$, R$^4$, R$^5$ and R$^6$ are preferably selected from hydrogen, lower alkyl, lower alkoxy or halogen.
Most preferred lower alkyl is methyl, most preferred lower alkoxy is methoxy and most preferred halogens are selected from fluorine, chlorine and bromine.

In one preferable embodiment, $R^2$, $R^3$, $R^4$ and $R^5$ are hydrogen and $R^6$ is lower alkyl, lower alkoxy or halogen, more preferably methyl, methoxy or chlorine.

In another preferable embodiment, $R^2$, $R^3$, $R^5$ and $R^6$ are hydrogen and $R^4$ is lower alkyl or halogen, more preferably methyl, fluorine, chlorine or bromine.

In another preferable embodiment, $R^2$, $R^4$ and $R^5$ are hydrogen and $R^3$ and $R^6$ are each independently lower alkyl or halogen, more preferably methyl, fluorine or chlorine.

Still in another preferable embodiment, $R^3$, $R^4$ and $R^5$ are hydrogen and $R^2$ and $R^6$ are each independently lower alkyl or halogen, more preferably methyl or chlorine.

In another embodiment the present invention relates to compounds of formula (I) for use in therapy, wherein $R^1$ is

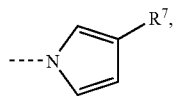

wherein $R^7$ is lower alkyl.

Preferable lower alkyl residues $R^7$ are methyl and ethyl, with methyl being especially preferred.

In another embodiment the present invention relates to compounds of formula (I) for use in therapy, wherein $R^1$ is

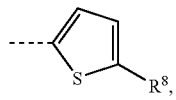

wherein $R^8$ is lower alkyl.

Preferable lower alkyl residue $R^8$ is methyl.

In another embodiment the present invention relates to compounds of formula (I) for use in therapy, wherein $R^1$ is

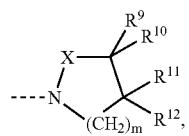

wherein X is >C=O or >$SO_2$;
$R^9$ and $R^{11}$ are hydrogen or together form a double bond;
$R^{10}$ and $R^{12}$ are independently selected from hydrogen or lower alkyl and
m is 1 or 2.

In one preferable embodiment X is >$SO_2$, $R^9$, $R^{10}$, $R^{11}$ and $R^{12}$ are hydrogen and m is 2.

In another preferable embodiment X is >C=O, $R^9$ and $R^{11}$ together form a double bond, $R^{10}$ and $R^{12}$ are hydrogen and m is 2.

In another preferable embodiment X is >C=O, $R^9$ and $R^{11}$ are hydrogen or together form a double bond, $R^{10}$ is lower alkyl, preferably methyl and $R^{12}$ is hydrogen and m is 1 or 2, more preferably 1.

Preferred compound of formula I for use in therapy are those, wherein n is 1.

Compounds of formula I, wherein n is 2, are also preferred for use in therapy.

Preferred compounds of the general formula I for use in therapy are those selected from the group consisting of:

(trans)-2-m-tolyl-cyclohexylamine,
(cis)-2-m-tolyl-cyclohexylamine,
(trans)-2-o-tolyl-cyclohexylamine,
(cis)-2-o-tolyl-cyclohexylamine,
(trans)-2-(2-methoxy-phenyl)-cyclohexylamine,
(trans)-2-(2,5-dichloro-phenyl)-cyclohexylamine,
(cis)-2-(2,5-dichloro-phenyl)-cyclohexylamine,
(trans)-2-(2,4-dimethyl-phenyl)-cyclohexylamine,
(cis)-2-(3-bromo-phenyl)-cyclohexylamine,
(trans)-2-(3-bromo-phenyl)-cyclohexylamine,
(trans)-2-(2-fluoro-5-methyl-phenyl)-cyclohexylamine,
(cis)-2-(5-methyl-thiophen-2-yl)-cyclohexylamine,
(trans)-2-(5-methyl-thiophen-2-yl)-cyclohexylamine,
(cis)-2-(2,4-dichloro-phenyl)-cyclohexylamine,
(trans)-2-(2,4-dichloro-phenyl)-cyclohexylamine,
(cis)-2-(3-fluoro-phenyl)-cyclohexylamine,
(trans)-2-(2-chloro-phenyl)-cyclohexylamine,
(trans)-2-(2,5-dimethyl-phenyl)-cyclohexylamine,
(cis/trans)-2-(2-fluoro-phenyl)-cyclohexylamine,
(trans)-2-(2-fluoro-phenyl)-cyclohexylamine,
(cis)-2-(3-chloro-phenyl)-cyclohexylamine,
(trans)-2-(3-chloro-phenyl)-cyclohexylamine,
(cis)-2-(2,5-dichloro-phenyl)-cycloheptylamine,
(trans)-2-(2,5-dichloro-phenyl)-cycloheptylamine,
(cis)-2-(2,5-dichloro-phenyl)-cyclopentylamine,
(trans)-2-(3-methyl-pyrrol-1-yl)-cyclohexylamine,
(trans)-2-(3-ethyl-pyrrol-1-yl)-cyclohexylamine,
(trans)-2-(1,1-dioxo-[1,2]thiazinan-2-yl)-cyclohexylamine,
(trans)-1-(2-amino-cyclohexyl)-5,6-dihydro-1H-pyridin-2-one,
(trans)-1-(2-amino-cyclohexyl)-4-methyl-1,5-dihydro-pyrrol-2-one,
(trans)-1-(2-amino-cyclohexyl)-4-methyl-5,6-dihydro-1H-pyridin-2-one,
(trans)-1-(2-amino-cyclohexyl)-piperidin-2-one,
(trans)-1-(2-amino-cyclohexyl)-4-methyl-pyrrolidin-2-one, and
pharmaceutically acceptable salts thereof.

The compounds of formula I have two or more asymmetric carbon atoms and can exist in the form of optically pure enantiomers, mixtures of diastereomers, racemates, or mixtures of diasteroisomeric racemates. The invention embraces all of these forms.

In a preferable embodiment, $R^1$ and the amino group in 1-position of the cycloalkylamine structure is in trans-configuration, i.e.

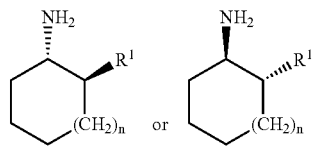

In a preferable embodiment, $R^1$ and the amino group in 1-position of the cycloalkylamine structure is in cis-configuration, i.e.

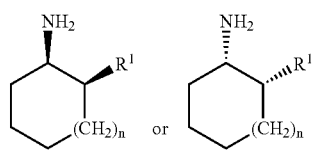

It will be appreciated, that the compounds of general formula (I) in this invention may be derivatized at functional groups to provide derivatives which are capable of converting back to the parent compound in vivo.

The present invention also relates to compounds of the formula (I)

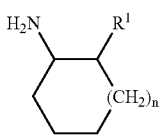

wherein
R¹ is selected from

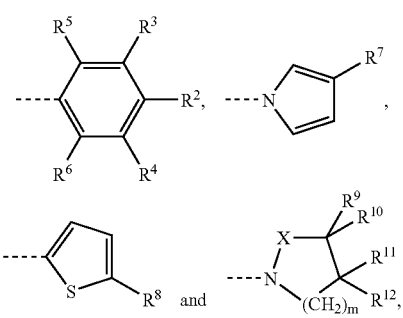

$R^2$, $R^3$, $R^4$, $R^5$ and $R^6$ are each independently selected from hydrogen, lower alkyl, halogenated lower alkyl or halogen; provided that $R^2$, $R^3$, $R^4$, $R^5$ and $R^6$ are not all hydrogen;
$R^7$ is lower alkyl;
$R^8$ is lower alkyl;
X is >C=O or >SO$_2$;
$R^9$ and $R^{11}$ are hydrogen or together form a double bond;
$R^{10}$ and $R^{12}$ are independently selected from hydrogen or lower alkyl;
m is 1 or 2;
n is 0, 1, or 2;
and pharmaceutically acceptable salts thereof,
with the further proviso that the following compounds are excluded:
2-(m-tolyl)-cyclohexylamine, 2-(p-tolyl)-cydohexylamine, 2-(o-tolyl)-cyclohexylamine, 2-(2-chlorophenyl)-cyclohexylamine, 2-(3-chlorophenyl)-cyclohexylamine, 2-(4-chlorophenyl)-cydohexylamine, 2-(2-bromophenyl)-cyclohexylamine, 2-(o-tolyl)-cyclopentylamine, 2-(p-tolyl)-cyclopentylamine,
2-(4-chlorophenyl)-cydopentylamine, 2-(3,5-difluorophenyl)-cyclopentylamine,
2-(3-fluorophenyl)-cyclopentylamine, 2-(4-fluorophenyl)-cyclopentylamine,
2-(4-bromophenyl)-cyclopentylamine, and 2-(4-tert-butylphenyl)-cydopentylamine.

2-(m-Tolyl)-cyclohexylamine and 2-(p-tolyl)-cyclohexylamine are described as intermediates for the synthesis of phenanthridine derivatives in J. Chem. Soc. 1956, 4280-4283. The synthesis of all isomeric forms of 2-(o-tolyl)-cyclohexylamine, 2-(p-tolyl)-cyclopentylamine, 2-(2-chlorophenyl)-cyclohexylamine, 2-(3-chlorophenyl)-cyclohexylamine and 2-(4-chlorophenyl)-cyclohexylamine for study of their proton magnetic resonance spectra is disclosed in J. Org. Chem. 1962, 27, 3006-3010. In J. Org. Chem. 1971, 36, 3046-3048 the synthesis of all isomers of 2-(2-bromophenyl)-cyclohexylamine and their NMR spectra are described.

2-(o-Tolyl)-cydopentylamine is known from WO 2004/016601 as reactant for the preparation of aminohydroxyalkybenzothiazolones useful as β3 adrenoreceptor agonists. 2-(p-Tolyl)-cyclopentylamine, 2-(4-chlorophenyl)-cydopentylamine, 2-(3,5-difluorophenyl)-cydopentylamine, 2-(3-fluorophenyl)-cyclopentylamine, 2-(4-fluorophenyl)-cyclopentylamine, 2-(4-bromophenyl)-cyclopentylamine and 2-(4-tert-butylphenyl)-cyclopentylamine are disclosed in WO 2001/042203 as intermediates for the synthesis of N-(phenylcyclopentyl)sulfonamides with glutamate receptor function potentiating activity.

Preferred compounds of formula I are those, wherein R¹ is

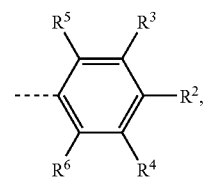

wherein $R^2$, $R^3$, $R^4$, $R^5$ and $R^6$ are each independently selected from hydrogen, lower alkyl, halogenated lower alkyl, lower alkoxy or halogen; provided that $R^2$, $R^3$, $R^4$, $R^5$ and $R^6$ are not all hydrogen.

$R^2$ preferably has the meaning of hydrogen, lower alkyl or halogen, more preferably of hydrogen, methyl or chlorine.

$R^3$, $R^4$, $R^5$ and $R^6$ are preferably selected from hydrogen, lower alkyl, lower alkoxy or halogen. Most preferred lower alkyl is methyl, most preferred lower alkoxy is methoxy and most preferred halogens are selected from fluorine, chlorine and bromine.

In one preferable embodiment, $R^2$, $R^3$, $R^4$ and $R^5$ are hydrogen and $R^6$ is lower alkyl, lower alkoxy or halogen, more preferably methyl, methoxy or chlorine.

In another preferable embodiment, $R^2$, $R^3$, $R^5$ and $R^6$ are hydrogen and $R^4$ is lower alkyl or halogen, more preferably methyl, fluorine, chlorine or bromine.

In another preferable embodiment, $R^2$, $R^4$ and $R^5$ are hydrogen and $R^3$ and $R^6$ are each independently lower alkyl or halogen, more preferably methyl, fluorine or chlorine.

Still in another preferable embodiment, $R^3$, $R^4$ and $R^5$ are hydrogen and $R^2$ and $R^6$ are each independently lower alkyl or halogen, more preferably methyl or chlorine.

Further preferred compounds of formula I of the present invention are those, wherein R¹ is

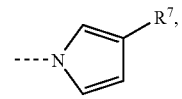

and wherein $R^7$ is lower alkyl.

Preferable lower alkyl residues $R^7$ are methyl and ethyl, with methyl being especially preferred.

In another embodiment of the present invention, compounds of formula I are those, wherein R¹ is

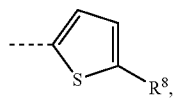

and wherein $R^8$ is lower alkyl.

Preferable lower alkyl residue $R^8$ is methyl.

Also preferred are compounds of formula I of the present invention, wherein $R^1$ is

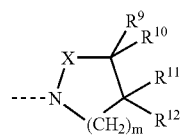

wherein X is >C=O or >SO$_2$;
$R^9$ and $R^{11}$ are hydrogen or together form a double bond;
$R^{10}$ and $R^{12}$ are independently selected from hydrogen or lower alkyl and
m is 1 or 2.

In one preferable embodiment X is >SO$_2$, $R^9$, $R^{10}$, $R^{11}$ and $R^{12}$ are hydrogen and m is 2.

In another preferable embodiment X is >C=O, $R^9$ and $R^{11}$ together form a double bond, $R^{10}$ and $R^{12}$ are hydrogen and m is 2.

In another preferable embodiment X is >C=O, $R^9$ and $R^{11}$ are hydrogen or together form a double bond, $R^{10}$ is lower alkyl, preferably methyl and $R^{12}$ is hydrogen and m is 1 or 2, more preferably 1.

Preferred compounds of formula I are those, wherein n is 1. Compounds of formula I, wherein n is 2, Especially preferred compounds of the general formula I are those selected from the group consisting of:
(trans)-2-(2-methoxy-phenyl)-cyclohexylamine,
(trans)-2-(2,5-dichloro-phenyl)-cyclohexylamine,
(cis)-2-(2,5-dichloro-phenyl)-cyclohexylamine,
(trans)-2-(2,4-dimethyl-phenyl)-cyclohexylamine,
(cis)-2-(3-bromo-phenyl)-cyclohexylamine,
(trans)-2-(3-bromo-phenyl)-cyclohexylamine,
(trans)-2-(2-fluoro-5-methyl-phenyl)-cyclohexylamine,
(cis)-2-(5-methyl-thiophen-2-yl)-cyclohexylamine,
(trans)-2-(5-methyl-thiophen-2-yl)-cyclohexylamine,
(cis)-2-(2,4-dichloro-phenyl)-cyclohexylamine,
(trans)-2-(2,4-dichloro-phenyl)-cyclohexylamine,
(cis)-2-(3-fluoro-phenyl)-cyclohexylamine,
(trans)-2-(2-chloro-phenyl)-cyclohexylamine,
(trans)-2-(2,5-dimethyl-phenyl)-cyclohexylamine,
(cis/trans)-2-(2-fluoro-phenyl)-cyclohexylamine,
(trans)-2-(2-fluoro-phenyl)-cyclohexylamine,
(cis)-2-(2,5-dichloro-phenyl)-cycloheptylamine,
(trans)-2-(2,5-dichloro-phenyl)-cycloheptylamine,
(cis)-2-(2,5-dichloro-phenyl)-cyclopentylamine,
(trans)-2-(3-methyl-pyrrol-1-yl)-cyclohexylamine,
(trans)-2-(3-ethyl-pyrrol-1-yl)-cydohexylamine,
(trans)-2-(1,1-dioxo-[1,2]thiazinan-2-yl)-cyclohexylamine,
(trans)-1-(2-amino-cyclohexyl)-5,6-dihydro-1H-pyridin-2-one,
(trans)-1-(2-amino-cyclohexyl)-4-methyl-1,5-dihydro-pyrrol-2-one,
(trans)-1-(2-amino-cyclohexyl)-4-methyl-5,6-dihydro-1H-pyridin-2-one,
(trans)-1-(2-amino-cyclohexyl)-piperidin-2-one,
(trans)-1-(2-amino-cyclohexyl)-4-methyl-pyrrolidin-2-one, and
pharmaceutically acceptable salts thereof.

The present invention also relates to a process for the manufacture of compounds of formula I.

In general the compounds of the formula I can be obtained either by a reductive amination of a ketone of formula II

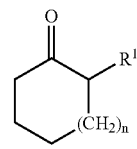

wherein $R^1$ and n are as defined above, or by deprotection of a carbamic acid ester of formula III

III

NHR$^P$ $R^1$ (CH$_2$)$_n$ wherein $R^1$ and n are as defined above and $R^P$ is an amino protecting group. $R^P$ is a suitable amino protecting group such as benzyloxycarbonyl (Z or Cbz), allyloxycarbonyl (Aloc), 9-fluorenylmethoxycarbonyl (Fmoc), and preferably, tert-butoxycarbonyl (Boc).

The compounds of formula (I) can be manufactured by the methods given below, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The compounds of the present invention can be prepared as illustrated in the schemes below:

Compounds of general formula Ia, in which $R^1$ is linked to the cycloalkane core through a carbon atom, are synthesized from a ketone II by methods known in the art such as by reductive amination using preferably ammonium acetate and sodium cyanoborohydride (Scheme 1)

Ketones of general formula II can be obtained from the respective alcohol e.g. by an oxidation using methods known in the art, preferably by using a Dess Martin Reagent. The alcohol itself can be obtained from the respective epoxide by methods known in the art, preferably using an organometallic reagent such as the suitable organo lithium reagent or the suitable Grignard reagent.

Scheme 1

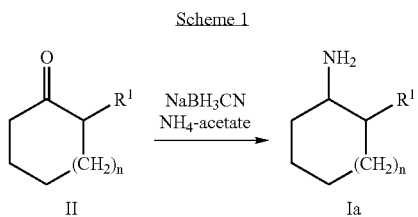

Compounds of general formula Ib, in which $R^1$ is linked to the cycloalkane core through a nitrogen atom can be synthesized from a carbamic acid ester III by methods known in the art. When $R^P$ is tert-butoxycarbonyl the reaction preferably is performed in the presence of hydrogen chloride in dioxane or with trifluoroacetic acid in dichloromethane. The carbamic acid ester III can be obtained from a carboxylic acid ester IV by hydrolysis and subsequent Curtius rearrangement, using methods known in the art (Scheme 2).

Scheme 2

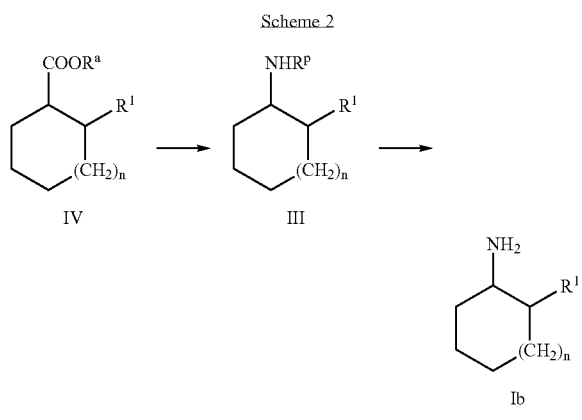

$R^a$ suitably is methyl or ethyl; $R^P$ is a suitable amino protecting group such as benzyloxycarbonyl, allyloxycarbonyl, and preferably, tert-butoxycarbonyl.

The synthesis of lactam or sultam derivatives Ic starts from cycloalkylamine V as shown below in scheme 3. V is reacted with an acid chloride or a sulfonyl chloride VII in the presence of a base (e. g., triethylamine) to afford amide or sulfonamide V. Then, cyclisation of V using a base, e.g., sodium hydride, in a solvent such as N,N-dimethylformamide, optionally in the presence of sodium iodide, leads to Ic. The carbamic acid ester can be transformed to the free amine as shown in scheme 2.

Scheme 3

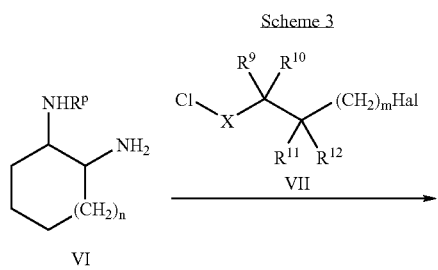

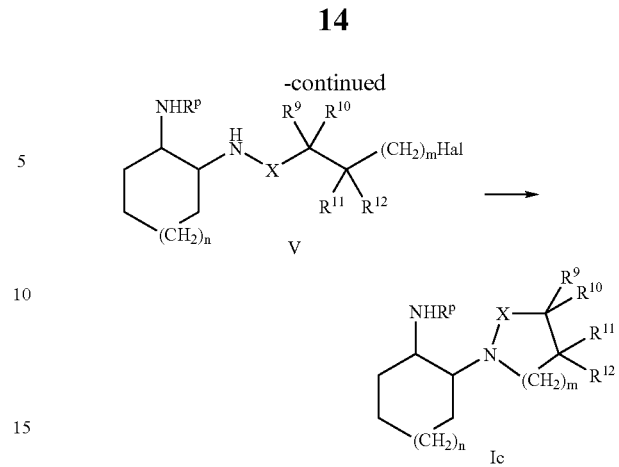

$R^P$ is a suitable amino protecting group such as benzyloxycarbonyl, allyloxycarbonyl, and, preferably, tert-butoxycarbonyl; Hal is a halogen, preferably chlorine The unsaturated lactams of the formula Ic wherein $R^9$ and $R^{10}$ form a double bond and X is >C=O can be synthesized from cycloalkylamine VI according to scheme 4. Thus, alkylation of VI with alkenyl halide IX (in the presence of a base, e. g., triethylamine), followed by acylation (in the presence of a base, e. g., triethylamine) with acyl halide IX, affords amide VIII. Compound VIII can then be is subjected to ring-closing metathesis (Acc. Chem. Res. 2001, 34, 18), using a ruthenium catalyst, e. g., bis(tricyclohexyl-phosphine)-benzylidene ruthenium(IV)dichloride, and optionally a Lewis acid, e. g., tetraisopropyl-orthotitanate, to afford Id. The carbamic acid ester can be transformed to the free amine as shown in scheme 2.

Scheme 4

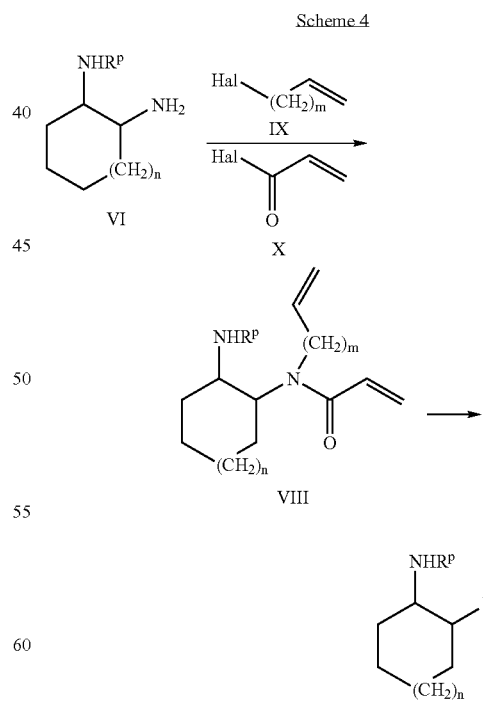

$R^P$ is a suitable amino protecting group such as benzyloxycarbonyl, allyloxycarbonyl, and, preferably, tert-butoxycarbonyl; Hal is a halogen, preferably chlorine The invention further relates to compounds of formula (I) as defined above, when manufactured according to a process as defined above.

As described above, the compounds of formula I of the present invention can be used as medicaments for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably non-insulin dependent diabetes mellitus and/or impaired glucose tolerance. Furthermore, the compounds of the present invention can be used as diuretic agents or for the treatment and/or prophylaxis of hypertension.

The invention therefore also relates to pharmaceutical compositions comprising a compound of formula I

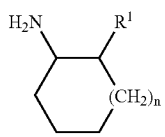

wherein
R$^1$ is selected from

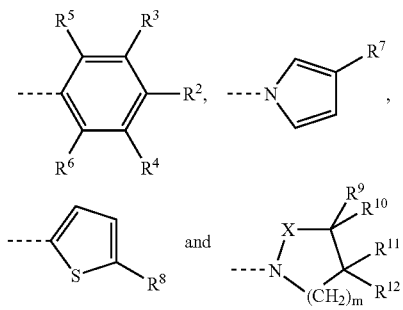

R$^2$, R$^3$, R$^4$, R$^5$ and R$^6$ are each independently selected from hydrogen, lower alkyl, halogenated lower alkyl, lower alkoxy or halogen; provided that R$^2$, R$^3$, R$^4$, R$^5$ and R$^6$ are not all hydrogen;
R$^7$ is lower alkyl;
R$^8$ is lower alkyl;
X is >C=O or >SO$_2$;
R$^9$ and R$^{11}$ are hydrogen or together form a double bond;
R$^{10}$ and R$^{12}$ are independently selected from hydrogen or lower alkyl;
m is 1 or 2; and
n is 0, 1, or 2;
or a pharmaceutically acceptable salt thereof;
and a pharmaceutically acceptable carrier and/or adjuvant.

Further, the invention relates to compounds as defined above for use as therapeutic active substances, particularly as therapeutic active substances for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for use as therapeutic active substances for the treatment and/or prophylaxis of non-insulin dependent diabetes mellitus and/or impaired glucose tolerance. Furthermore, the invention relates to compounds as defined above for use as diuretic agents or for use as therapeutic active substances for the treatment and/or prophylaxis of hypertension.

In another embodiment, the invention relates to a method for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance, which method comprises administering a compound as defined above to a human being or animal. Furthermore, the invention relates to a method for the treatment and/or prophylaxis as defined above, wherein the disease is hypertension or wherein a diuretic agent has a beneficial effect.

The invention further relates to the use of compounds as defined above for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance. Furthermore, the invention relates to the use as defined above, wherein the disease is hypertension or to the use as diuretic agent.

In addition, the invention relates to the use of compounds as defined above for the preparation of medicaments for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance. Such medicaments comprise a compound as defined above. Furthermore, the invention relates to the use as defined above, wherein the disease is hypertension or the use for the preparation of diuretic agents.

In context with the methods and uses defined above, the following diseases relate to a preferred embodiment: diabetes, particularly non-insulin dependent diabetes mellitus, impaired glucose tolerance, obesity, and/or metabolic syndrome or β-cell protection, preferably non-insulin dependent diabetes mellitus and/or impaired glucose tolerance.

The following tests were carried out in order to determine the activity of the compounds of formula I.

Activity of DPP-IV inhibitors are tested with natural human DPP-IV derived from a human plasma pool or with recombinant human DPP-IV. Human citrate plasma from different donors is pooled, filtered through a 0.2 micron membrane under sterile conditions and aliquots of 1 ml are shock frozen and stored at −120° C. until used. In the colorimetric DPP-IV assay 5 to 10 μl human plasma and in the fluorometric assay 1.0 μl of human plasma in a total assay volume of 100 μl is used as an enzyme source. The cDNA of the human DPP-IV sequence of amino acid 31- to 766, restricted for the N-terminus and the transmembrane domain, is cloned into Pichia pastoris. Human DPP-IV is expressed and purified from the culture medium using conventional column chromatography including size exclusion and anion and cation chromatography. The purity of the final enzyme preparation of Coomassie blue SDS-PAGE is >95%. In the colorimetric DPP-IV assay 20 ng rec.-h DPP-IV and in the fluorometric assay 2 ng rec-h DPP-IV in a total assay volume of 100 μl is used as an enzyme source.

In the fluorogenic assay Ala-Pro-7-amido-4-trifluoromethylcoumarin (Calbiochem No 125510) is used as a substrate. A 20 mM stock solution in 10% DMF/H$_2$O is stored at −20° C. until use. In IC$_{50}$ determinations a final substrate concentration of 50 μM is used. In assays to determine kinetic parameters as $K_m$, $V_{max}$, $K_i$, the substrate concentration is varied between 10 μM and 500 μM.

In the colorimetric assay H-Ala-Pro-pNA.HCl (Bachem L-11115) is used as a substrate. A 10 mM stock solution in 10% MeOH/H$_2$O is stored at −20° C. until use. In IC$_{50}$ determinations a final substrate concentration of 200 μM is used. In assays to determine kinetic parameters as $K_m$, $V_{max}$, $K_i$, the substrate concentration is varied between 100 μM and 2000 μM.

Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA liberated from the colorimetric substrate is detected in a Packard SpectraCount at 405 nm continuously every 2 minutes for 30 to 120 minutes. Initial rate constants are calculated by best fit linear regression.

DPP-IV activity assays are performed in 96 well plates at 37° C. in a total assay volume of 100 μl. The assay buffer consists of 50 mM Tris/HCl, pH 7.8 containing 0.1 mg/ml BSA and 100 mM NaCl. Test compounds are solved in. 100% DMSO, diluted to the desired concentration in 10% DMSO/H$_2$O. The final DMSO concentration in the assay is 1% (v/v). At this concentration enzyme inactivation by DMSO is <5%. Compounds are with (10 minutes at 37° C.) and without preincubation with the enzyme. Enzyme reactions are started with substrate application followed by immediate mixing.

IC$_{50}$ determinations of test compounds are calculated by non-linear best fit regression of the DPP-IV inhibition of at least 5 different compound concentrations. Kinetic parameters of the enzyme reaction are calculated at least 5 different substrate concentrations and at least 5 different test compound concentrations.

The compounds of the present invention exhibit IC$_{50}$ values of 0.1 μM to 50 μM, more preferably of 0.1 μM to 1 μM as shown in the following table:

| Example | IC$_{50}$ [μM] |
|---------|----------------|
| 7       | 0.13           |
| 18      | 0.16           |
| 24      | 0.72           |
| 30      | 0.73           |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varyi ng the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Example 1 and 2

(trans)-2-m-tolyl-cyclohexylamine and (cis)-2-m-tolyl-cyclohexylamine

To a solution of 1-bromo-3-methyl-benzene in THF at −78° C., was added dropwise a solution of nBuLi (1.6M in THF, 12.4 ml) and the reaction mixture was stirred at −78° C. for 30 minutes. After such time, 7-oxa-bicyclo[4.1.0]heptane (3.4 g) was added slowly to the reaction mixture followed by the addition of boron trifluoride etherate (2.5 ml). The reaction mixture was stirred at −78° C. for another 2 hours before allowing it to warm up to room temperature. The solution was then treated with solution of ammonium chloride (25 ml), the phases were separated and then extracted twice with ethyl acetate. The combined organic extracts were then washed with water, dried over sodium sulfate and concentrated in vacuo. The residue was then purified by column chromatography to give 2.9 g of (cis/trans) 2-o-tolyl-cyclohexanol MS(EI) 190.1 (M⁺).

To (cis/trans) 2-o-tolyl-cyclohexanol (1 g) in dichloromethane (30 ml) was added Dess-Martin periodinane (Aldrich 27,462-3) at room temperature. The reaction mixture was allowed to stir at room temperature for 16 hours before diethyl ether was added. The volume of solvent was reduced in vacuo to about one quarter of the initial amount. More diethylether (87 ml) was added and the solution was washed with a 10% solution of sodium thiosulfate (87 ml), a solution of saturated sodium bicarbonate (87 ml), brine (100 mL) and water (100 ml). The organic phase was then dried over sodium sulfate and concentrated in vacuo. The residue was then purified by column chromatography to give 0.54 g of 2-o-tolyl-cyclohexanone MS (EI) 188.2 (M⁺).

To 2-o-tolyl-cyclohexanone (0.22 g) in methanol (30 ml) was added ammonium acetate (0.90 g) and the reaction was allowed to stir at room temperature for 16 hours. After such time sodiumcyanoborohydride (91 mg) was added to the reaction mixture and stirred for 10 minutes. The reaction mixture was then treated with a saturated aqueous solution of NaHCO₃, and extracted with ethyl acetate (2×50 ml). The combined organic phases were dried over sodium sulfate, concentrated in vacuo and purified by column chromatography to yield (cis) 2-m-tolyl-cyclohexylamine (35 mg) MS(ISP) 190.3 (M+H)⁺ and (trans) 2-m-tolyl-cyclohexylamine MS(ISP) 190.3 (M⁺H)⁺.

The following examples were prepared in analogy to Examples 1 and 2:

| Ex. | Systematic name | Starting material | MW | MW (found) (MH⁺) |
|---|---|---|---|---|
| 3 | (trans)-2-o-Tolyl-cyclohexylamine | 1-Bromo-2-methyl-benzene | 189.3 | 190.2 |
| 4 | (cis)-2-o-Tolyl-cyclohexylamine | 1-Bromo-2-methyl-benzene | 189.3 | 190.2 |
| 5 | (trans)-2-(2-Methoxy-phenyl)-cyclohexylamine | 1-Bromo-2-methoxy-benzene | 205.3 | 206.1 |
| 6 | (trans)-2-(2,5-Dichloro-phenyl)-cyclohexylamine | 2-Bromo-1,4-dichloro-benzene | 244.2 | 244.2 |
| 7 | (cis)-2-(2,5-Dichloro-phenyl)-cyclohexylamine | 2-Bromo-1,4-dichloro-benzene | 244.2 | 244.2 |
| 8 | (trans)-2-(2,4-Dimethyl-phenyl)-cyclohexylamine | 1-Bromo-2,4-dimethyl-benzene | 203.3 | 204.1 |
| 9 | (cis)-2-(3-Bromo-phenyl)-cyclohexylamine | 1,3-Dibromo-benzene | 254.2 | 254.0 |
| 10 | (trans)-2-(3-Bromo-phenyl)-cyclohexylamine | 1,3-Dibromo-benzene | 254.2 | 254.0 |
| 11 | (trans)-2-(2-Fluoro-5-methyl-phenyl)-cyclohexylamine | 2-Bromo-1-fluoro-4-methyl-benzene | 207.3 | 244.2 |
| 12 | (cis)-2-(5-Methyl-thiophen-2-yl)-cyclohexylamine | 2-Bromo-5-methyl-thiophene | 195.3 | 196.2 |
| 13 | (trans)-2-(5-Methyl-thiophen-2-yl)-cyclohexylamine | 2-Bromo-5-methyl-thiophene | 195.3 | 196.1 |
| 14 | (cis)-2-(2,4-Dichloro-phenyl)-cyclohexylamine | 1-Bromo-2,4-dichloro-benzene | 244.2 | 244.2 |
| 15 | (trans)-2-(2,4-Dichloro-phenyl)-cyclohexylamine | 1-Bromo-2,4-dichloro-benzene | 244.2 | 244.2 |
| 16 | (cis)-2-(3-Fluoro-phenyl)-cyclohexylamine | 1-Bromo-3-fluoro-benzene | 193.3 | 194.2 |
| 17 | (trans)-2-(2-Chloro-phenyl)-cyclohexylamine | 1-Chloro-2-iodo-benzene | 209.7 | 210.2 |
| 18 | (trans)-2-(2,5-Dimethyl-phenyl)-cyclohexylamine | 2-Bromo-1,4-dimethyl-benzene | 203.3 | 204.3 |
| 19 | (cis/trans)-2-(2-Fluoro-phenyl)-cyclohexylamine | 1-Bromo-2-fluoro-benzene | 193.3 | 194.3 |
| 20 | (trans)-2-(2-Fluoro-phenyl)-cyclohexylamine | 1-Bromo-2-fluoro-benzene | 193.3 | 194.2 |
| 21 | (cis)-2-(3-Chloro-phenyl)-cyclohexylamine | 1-Bromo-3-chloro-benzene | 209.7 | 210.2 |
| 22 | (trans)-2-(3-Chloro-phenyl)-cyclohexylamine | 1-Bromo-3-chloro-benzene | 209.7 | 210.2 |
| 23 | (cis)-2-(2,5-Dichloro-phenyl)-cycloheptylamine | 2-Bromo-1,4-dichloro-benzene and 8-Oxa-bicyclo[5.1.0]octane | 258.2 | 258.1 |
| 24 | (trans)-2-(2,5-Dichloro-phenyl)-cycloheptylamine | 2-Bromo-1,4-dichloro-benzene and 8-Oxa-bicyclo[5.1.0]octane | 258.2 | 258.1 |
| 25 | (cis)-2-(2,5-Dichloro-phenyl)-cyclopentylamine | 2-Bromo-1,4-dichloro-benzene and 6-Oxa-bicyclo[3.1.0]hexane | 230.1 | 230.1 |

Example 26

(trans)-2-(3-Methyl-pyrrol-1-yl)-cyclohexylamine trans-[2-(3-Formyl-pyrrol-1-yl)-cyclohexyl]-carbamic acid tert-butyl ester A solution of trans-(2-amino-cyclohexyl)-carbamic acid tert-butyl ester (*Tetrahedron Lett*. 2000, 41, 9607; 400 mg, 1.87 mmol) and 2,5-dimethoxy-3-tetrahydrofurancarboxaldehyde (365 mg, 2.05 mmol) in pyridine (0.5 mL) and acetic acid (0.82 mL) was heated at 100° C. for 4.5 h. After cooling, the reaction mixture was partitioned between ethyl acetate and 10% aq. citric acid solution. The organic layer was washed with brine, dried (MgSO₄), and evaporated. Chromatography (SiO₂, heptane-ethyl acetate gradient) yielded the title compound (334 mg, 61%). Off-white solid, MS (ISP) 293.3 (M⁺H)⁺.

trans-2-(3-Methyl-pyrrol-1-yl)-cyclohexylamine

Triethylsilane (368 mg, 3.16 mmol) was added at 0° C. to a solution of trans-[2-(3-formyl-pyrrol-1-yl)-cyclohexyl]-carbamic acid tert-butyl ester (330 mg, 1.13 mmol) in trifluoroacetic acid (5.1 ml), then after 90 min the reaction mixture was evaporated and partitioned between ethyl acetate and 2 M aq. sodium hydroxide solution. The organic layer was washed with brine, dried (MgSO₄), and evaporated. Chromatography (SiO₂, CH₂Cl₂/MeOH/NH₄OH 90:10:0.25) yielded the title compound (163 mg, 81%). Yellow oil, MS (ISP) 179.1 (M⁺H)⁺.

Example 27 trans-2-(3-Ethyl-pyrrol-1-yl)-cyclohexylamine trans-[2-(3-Ethyl-pyrrol-1-yl)-cydohexyl]-carbamic acid tert-butyl ester Methylmagnesium chloride solution (3 M in tetrahydrofuran, 0.23 ml, 0.68 mmol) was added at −78° C. to a solution of trans-[2-(3-formyl-pyrrol-1-yl)-cyclohexyl]-carbamic acid tert-butyl ester (example 26a, 100 mg, 0.34 mmol) in tetrahydrofuran (2 ml), then after 3.5 h the reaction was quenched by addition of saturated aqueous ammonium chloride solution and extracted with dichloromethane. The organic layer was washed with brine, dried (MgSO₄), and evaporated. This crude material (103 mg) was dissolved in dichloromethane (2 ml) and treated with triethylsilane (58 mg, 0.50 mmol) and trifluoroacetic acid (190 mg, 1.67 mmol). The reaction mixture was allowed to reach 0° C. over 3 h, then evaporated and the residue chromatographed (SiO$_2$, heptane-ethyl acetate gradient) to afford the title compound (27 mg, 28%). Yellow solid, MS (ISP) 293.2 (M$^+$H)$^+$.

trans-2-(3-Ethyl-pyrrol-1-yl)-cyclohexylamine

A solution of trans-[2-(3-ethyl-pyrrol-1-yl)-cyclohexyl]-carbamic acid tert-butyl ester (24 mg, 82 μmol) in hydrochloric acid solution (4 M in 1,4-dioxane) was stirred for 90 min at room temperature, then evaporated. The residue was taken up in CH$_2$Cl$_2$/MeOH/NH$_4$OH 90:10:0.25 and the solution concentrated in vacuo. Chromatography (SiO$_2$, CH$_2$Cl$_2$/MeOH/NH$_4$OH 90:10:0.25) afforded the title compound (5 mg, 32%). Light yellow solid, MS (ISP) 193.4 (M$^+$H)$^+$.

Example 28 trans-2-(1,1-Dioxo-[1,2]thiazinan-2-yl)-cyclohexylamine trans-[2-(4-Chloro-butane-1-sulfonylamino)-cyclohexyl]-carbamic acid tert-butyl ester 4-Chlorobutanesulfonyl chloride (178 mg, 0.93 mmol). was added at 0° C. to a solution of trans-(2-amino-cyclohexyl)-carbamic acid tert-butyl ester (200 mg, 0.93 mmol) and triethylamine (94 mg, 0.93 mmol) in dichloromethane (2 ml), and the reaction mixture was allowed to reach room temperature over 3 h, then partitioned between dichloromethane and 10% aq. citric acid solution. The organic layer was washed with 1 M aq. sodium carbonate solution and brine, dried (MgSO$_4$), and evaporated. Chromatography (SiO$_2$, heptane-ethyl acetate gradient) afforded the title compound (130 mg, 38%). Off-white solid, MS (ISP) 367.2 (M−H)$^-$.

trans-2-(1,1-Dioxo-[1,2]thiazinan-2-yl)-cyclohexylamine

Sodium hydride (60% dispersion in mineral oil, 15 mg, 0.38 mmol) was added at 0° C. to a solution of trans-[2-(4-chloro-butane-1-sulfonylamino)-cyclohexyl]-carbamic acid tert-butyl ester (125 mg, 0.34 mmol) and sodium iodide (51 mg, 0.34 mmol), and the reaction mixture was stirred at room temperature for 24 h, then another portion of sodium hydride (15 mg, 0.38 mmol) was added, and the reaction mixture was heated at 60° C. for 3 h. After cooling, the solution was partitioned between heptane/ethyl acetate (1:1) and water. The organic layer was washed with brine, evaporated, and chromatographed (SiO$_2$, heptane-ethyl acetate gradient). The title compound was obtained from this material in accordance with the general method of example 27b. Off-white solid, MS (ISP) 233.1 (M$^+$H)$^+$.

Example 29 trans-1-(2-Amino-cyclohexyl)-5,6-dihydro-1H-pyridin-2-one trans-(2-But-3-enylamino-cyclohexyl)-carbamic acid tert-butyl ester The title compound was produced in accordance with the general method of example 30a from trans-(2-amino-cyclohexyl)-carbamic acid tert-butyl ester and 4-bromo-1-butene. Brown solid, MS (ISP) 269.3 (M+H)$^+$.

trans-[2-(Acryloyl-but-3-enyl-amino)-cyclohexyl]-carbamic acid tert-butyl ester

Acryloyl chloride (47 mg, 0.50 mmol) was added at 0° C. to a solution of trans-(2-but-3-enylamino-cyclohexyl)-carbamic acid tert-butyl ester (123 mg, 0.46 mmol) and triethylamine (51 mg, 0.51 mmol) in dichloromethane (3 ml), and the reaction mixture was allowed to reach room temperature over 3 h. After partitioning between dichloro-methane and 10% aq. citric acid solution, the organic layer was washed with 1 M aq. sodium carbonate solution and brine, dried (MgSO$_4$), and evaporated. Chromatography (SiO$_2$, heptane-ethyl acetate gradient) afforded the title compound (103 mg, 70%). Light yellow solid, MS (ISP) 323.3 (M$^+$H)$^+$.

trans-[2-(6-Oxo-3,6-dihydro-2H-pyridin-1-yl)-cyclohexyl]-carbamic acid tert-butyl ester Bis(tricyclohexylphosphine)benzylidene ruthenium(IV) dichloride (13 mg, 16 μmol) was added to a solution of trans-[2-(acryloyl-but-3-enyl-amino)-cyclohexyl]-carbamic acid tert-butyl ester (50 mg, 0.16 mmol) and tetraisopropyl orthotitanate (8.8 mg, 31 μmol) in dichloromethane (2.5 ml), and the reaction mixture was stirred for 1 h at room temperature. The solvent was then evaporated and the residue chromatographed (SiO$_2$, heptane-ethyl acetate gradient) to produce the title compound (44 mg, 96%). Off-white solid, MS (ISP) 295.2 (M$^+$H)$^+$.

trans-1-(2-Amino-cyclohexyl)-5,6-dihydro-1H-pyridin-2-one

The title compound was produced in accordance with the general method of example 27b from trans-[2-(6-oxo-3,6-dihydro-2H-pyridin-1-yl)-cyclohexyl]-carbamic acid tert-butyl ester. Light yellow liquid, MS (ISP) 195.3 (M$^+$H)$^+$.

Example 30 trans-1-(2-Amino-cyclohexyl)-4-methyl-1,5-dihydro-pyrrol-2-one trans-[2-(2-Methyl-allylamino)-cyclohexyl]-carbamic acid tert-butyl ester Methallyl bromide (139 mg, 1.03 mmol) was added at 0° C. to a solution of trans-(2-amino-cyclohexyl)-carbamic acid tert-butyl ester (200 mg, 0.93 mmol) and triethylamine (113 mg, 1.12 mmol) in tetrahydrofuran (4 ml). The reaction mixture was stirred for 16 h at room temperature, then partitioned between ethyl acetate and 1 M aq. sodium hydroxide solution. The organic layer was washed with brine, dried (MgSO$_4$), and evaporated. Chromatography (SiO$_2$, CH$_2$Cl$_2$/MeOH/NH$_4$OH 90:10:0.25) afforded the title compound (177 mg, 71%). Orange solid, MS (ISP) 269.3 (M$^+$H)$^+$.

trans-{2-[Acryloyl-(2-methyl-allyl)-amino]-cyclohexyl}-carbamic acid tert-butyl ester The title compound was produced in accordance with the general method of example 29b from trans-[2-(2-methyl-allylamino)-cyclohexyl]-carbamic acid tert-butyl ester and acryloyl chloride. Off-white solid, MS (ISP) 323.3 (M$^+$H)$^+$.

trans-[2-(4-Methyl-2-oxo-2,5-dihydro-pyrrol-1-yl)-cyclohexyl]-carbamic acid tert-butyl ester The title compound was produced in accordance with the general method of example 31c from trans-{2-[acryloyl-(2-methyl-allyl)-amino]-cyclohexyl}-carbamic acid tert-butyl ester. Black solid, MS (ISP) 295.2 (M$^+$H)$^+$.

trans-1-(2-Amino-cyclohexyl)-4-methyl-1,5-dihydro-pyrrol-2-one

The title compound was produced in accordance with the general method of example 27b from trans-[2-(4-methyl-2-oxo-2,5-dihydro-pyrrol-1-yl)-cyclohexyl]-carbamic acid tert-butyl ester. Yellow solid, MS (ISP) 195.2 $(M^+H)^+$.

Example 31 trans-1-(2-Amino-cyclohexyl)-4-methyl-5,6-dihydro-1H-pyridin-2-one trans-[2-(3-Methyl-but-3-enylamino)-cyclohexyl]-carbamic acid tert-butyl ester The title compound was produced in accordance with the general method of example 30a from trans-(2-amino-cyclohexyl)-carbamic acid tert-butyl ester and 4-bromo-2-methyl-1-butene (*J. Org. Chem.* 1997, 62, 1536). Brown solid, MS (ISP) 283.3 $(M^+H)^+$.

trans-{2-[Acryloyl-(3-methyl-but-3-enyl)-amino]-cyclohexyl}-carbamic acid tert-butyl ester The title compound was produced in accordance with the general method of example 29b from trans-[2-(3-methyl-but-3-enylamino)-cyclohexyl]-carbamic acid tert-butyl ester and acryloyl chloride. Off-white solid, MS (ISP) 337.4 $(M^+H)^+$.

trans-[2-(4-Methyl-6-oxo-3,6-dihydro-2H-pyridin-1-yl)-cyclohexyl]-carbamic acid tert-butyl ester Dichloro(1,3-dimesityl-4,5-dihydroimidazol-2-ylidene)(phenylmethylene)-(tricyclohexylphosphine)ruthenium (54 mg, 63 µmol) was added to a solution of trans-{2-[acryloyl-(3-methyl-but-3-enyl)-aminol-cyclohexyl}-carbamic acid tert-butyl ester (212 mg, 0.63 mmol) and tetraisopropyl orthotitanate (36 mg, 0.13 mmol) in chloroform (11 ml), and the reaction mixture was heated at reflux for 72 h. The solvent was then evaporated and the residue chromatographed (SiO$_2$, heptane-ethyl acetate gradient) to produce the title compound (120 mg, 62%). Off-white solid, MS (ISP) 309.1 $(M^+H)^+$.

trans-1-(2-Amino-cyclohexyl)-4-methyl-5,6-dihydro-1H-pyridin-2-one

The title compound was produced in accordance with the general method of example 27b from trans-[2-(4-methyl-6-oxo-3,6-dihydro-2H-pyridin-1-yl)-cyclohexyl]-carbamic acid tert-butyl ester. Brown liquid, MS (ISP) 209.2 $(M^+H)^+$.

Example 32 trans-1-(2-Amino-cyclohexyl)-piperidin-2-one

The title compound was produced in accordance with the general method of example 28 from trans-(2-amino-cyclohexyl)-carbamic acid tert-butyl ester and 5-chlorovaleroyl chloride. Colorless liquid, MS (ISP) 197.2 $(M^+H)^+$.

Example 33

1-(2-Amino-cyclohexyl)-4-methyl-pyrrolidin-2-one cis-2-(4-Chloro-3-methyl-butyrylamino)-cyclohexanecarboxylic acid ethyl ester Preparation of ethyl cis-2-amino-1-cyclohexanecarboxylate:

Ethyl-cis-2-amino-1-cyclohexanecarboxylate hydrochloride (750 mg) was suspended in 1 N NaOH (pH =12). The aqueous layer was extracted with CH$_2$Cl$_2$, washed with brine, dried over Na$_2$SO$_4$ and evaporated to give the crude ethyl-cis-2-amino-1-cyclohexanecarboxylate (570 mg).

The crude ethyl-cis-2-amino-1-cyclohexanecarboxylate (570 mg) was dissolved in CH$_2$Cl$_2$ (15 ml) under argon and cooled to 0° C. by means of an ice bath. Triethylamine (0.51 ml) was then added dropwise over a period of 10 min. The mixture was then stirred for 30 min and then treated with 4-chloro-3-methyl-butyryl chloride (568 mg), synthesized according to Chem. Ber., 97, 1964, 2544-2550 dropwise over a period of 10 min; a white suspension was obtained. The resulting mixture was allowed to RT and stirred for 30 min. The mixture was poured into ice/brine and the aqueous layer was extracted with ethyl acetate. The organic layer was separated, washed with brine, dried over Na$_2$SO$_4$ and evaporated. The residue was purified by flash chromatography (heptane/ethyl acetate 7:3) to give the product as a 1:1 mixture of epimers as a light yellow oil (913 mg). MS (ESI): 290.1 $(M^+H^+)$.

trans-2-(4-Methyl-2-oxo-pyrrolidin-1-yl)-cyclohexanecarboxylic acid ethyl ester cis-2-(4-Chloro-3-methyl-butyrylamino)-cyclohexanecarboxylic acid ethyl ester (895 mg) was dissolved in absolute DMF (20 ml) under argon at RT. Sodium iodide (463 mg) and sodium hydride (55%) (270 mg) were added; a white suspension was obtained. The mixture was then stirred for 2 hours at room temperature. The reaction mixture was poured into ice/water containing saturated NH$_4$Cl solution and the aqueous layer was extracted with ethyl acetate. The organic layer was separated, washed with brine, dried over Na$_2$SO$_4$ and evaporated. The residue was purified by flash chromatography (CH$_2$Cl$_2$/MeOH/NH$_3$ 95/5/0.5) to give the product as a 1:1 mixture of epimers as a light yellow liquid (402 mg). MS (ESI): 254.1 $(M^+H^+)$.

trans-2-(4-Methyl-2-oxo-pyrrolidin-1-yl)-cyclohexanecarboxylic acid trans-2-(4-Methyl-2-oxo-pyrrolidin-1-yl)-cyclohexanecarboxylic acid ethyl ester (395 mg) was dissolved in absolute THF (15 ml) and 1 N lithium hydroxide solution (5.12 ml) was added. The resulting mixture was refluxed over night. The reaction mixture was cooled to room temperature and then HCl conc. (1.80 ml) was added (pH=2). The mixture was evaporated and then diluted with toluene and evaporated to remove the water. The residue was purified by flash chromatography (AcOEt/MeOH 85/15) to give the product as a 1:1 mixture of epimers as light yellow foam (435 mg). MS (ESI): 224.3 $(M^+H^{+-})$.

trans-2-(4-Methyl-2-oxo-pyrrolidin-1-yl)-cyclohexyl]-carbamic acid benzyl ester trans-2-(4-Methyl-2-oxo-pyrrolidin-1-yl)-cyclohexanecarboxylic acid (100 mg), diphenylphosphorylazide (DPPA) (183 mg), benzylalcohol (0.686 ml) and triethylamine (0.062 ml) were dissolved in absolute toluene (1.0 ml) and the mixture was then heated to 80° C. over night. The reaction mixture was then directly evaporated. The residue was purified by flash-chromatography (AcOEt/heptane 80/20) to give the compound as a 1:1 mixture of epimers as white foam (42 mg). MS (ESI): 331.2 $(M^+H^+)$.

trans-1-(2-Amino-cyclohexyl)-4-methyl-pyrrolidin-2-one

To a solution of trans-[2-(4-methyl-2-oxo-pyrrolidin-1-yl)-cydohexyl]-carbamic acid benzyl ester (34 mg) in absolute ethanol (4.0 ml) was added 10% Pd on charcoal (5 mg). A hydrogen atmosphere was introduced by repeated evacuation/gas introduction. The suspension was vigorously stirred over night. The catalyst was removed by filtration through dicalite and the filtrate was concentrated in vacuo. The residue was purified by flash chromatography ($CH_2Cl_2$/MeOH/$NH_3$ 93/7/0.5) to give the product as a 1:1 mixture of epimers as a colorless liquid (15 mg). MS (ESI): 197.3 ($M^+H^+$).

Example 34

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example 35

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 36

Injection solutions can have the following composition:

| Ingredients | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example 37

Soft gelatin capsules containing the following ingredients can be manufactured in a conventional manner:

| Ingredients | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 38

Sachets containing the following ingredients can be manufactured in a conventional manner:

| Ingredients | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound according to formula (I):

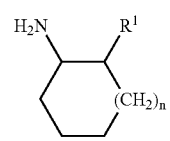

wherein:

R¹ is selected from

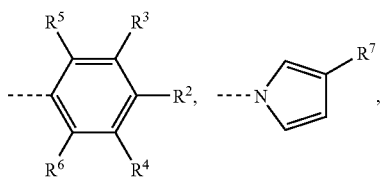

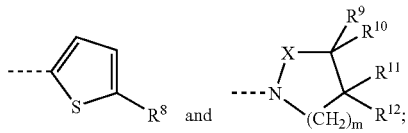

R², R³, R⁴, R⁵ and R⁶ are each independently selected from hydrogen, lower alkyl, halogenated lower alkyl or halogen; provided that R², R³, R⁴, R⁵ and R⁶ are not all hydrogen;

R⁷ is lower alkyl;

R⁸ is lower alkyl;

X is >C=O or >SO₂;

R⁹ R¹¹ are hydrogen or together form a double bond;

R¹⁰ and R¹² are independently selected from hydrogen or lower alkyl;

m is 1 or 2;

n is 0, 1, or 2;

and pharmaceutically acceptable salts thereof, with the further proviso that the following compounds are excluded 2-(m-tolyl)-cyclohexylamine, 2-(p-tolyl)-cyclohexylamine, 2-(o-tolyl)-cyclohexylamine, 2-(2-chlorophenyl)-cyclohexylamine, 2-(3-chlorophenyl)-cyclohexylamine, 2-(p-chlorophenyl)-cyclohexylamine, 2-(2-bromophenyl)-cyclohexylamine, 2-(o-tolyl)-cyclopentylamine, 2-(p-tolyl)-cyclopentylamine, 2-(4-chlorophenyl)-cyclopentylamine, 2-(3,5-difluorophenyl)-cyclopentylamine, 2-(3-fluorophenyl)-cyclopentylamine, 2-(4-fluorophenyl)-cyclopentylamine, 2-(4-bromophenyl)-cyclopentylamine, 2-(4-tert-butylphenyl)-cyclopentylamine, and 2-(3,4-difluorophenyl)-cyclopentylamine.

2. The compound according to claim 1, wherein R¹ is

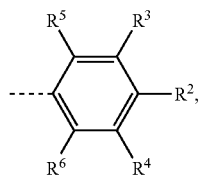

and wherein R², R³, R⁴, R⁵ and R⁶ are each independently selected from hydrogen, lower alkyl, halogenated lower alkyl, lower alkoxy or halogen; provided that R², R³, R⁴, R⁵ and R⁶ are not all hydrogen.

3. The compound according to claim 1, wherein R¹ is

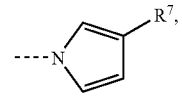

and wherein R⁷ is lower alkyl.

4. The compound according to claim 1, wherein R¹ is

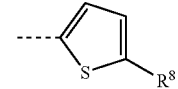

and wherein R⁸ is lower alkyl.

5. The compound according to claim 1, wherein R¹ is

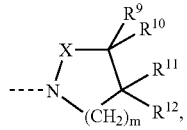

X is >C=O or >SO₂;

R⁹ and R¹¹ are hydrogen or together form a double bond;

R¹⁰ and R¹² are independently selected from hydrogen or lower alkyl and m is 1 or 2.

6. The compound according to claim 1 selected from
(trans)-2-m-tolyl-cyclohexylamine,
(cis)-2-m-tolyl-cyclohexylamine,
(trans)-2-o-tolyl-cyclohexylamine,
(cis)-2-o-tolyl-cyclohexylamine,
(trans)-2-(2-methoxy-phenyl)-cyclohexylamine,
(trans)-2-(2,5-dichloro-phenyl)-cyclohexylamine,
(cis)-2-(2,5-dichloro-phenyl)-cyclohexylamine,
(trans)-2-(2,4-dimethyl-phenyl)-cyclohexylamine,
(cis)-2-(3-bromo-phenyl)-cyclohexylamine,
(trans)-2-(3-bromo-phenyl)-cyclohexylamine,
(trans)-2-(2-fluoro-5-methyl-phenyl)-cyclohexylamine,
(cis)-2-(5-methyl-thiophen-2-yl)-cyclohexylamine,
(trans)-2-(5-methyl-thiophen-2-yl)-cyclohexylamine,
(cis)-2-(2,4-dichloro-phenyl)-cyclohexylamine,
(trans)-2-(2,4-dichloro-phenyl)-cyclohexylamine,
(cis)-2-(3-fluoro-phenyl)-cyclohexylamine,
(trans)-2-(2-chloro-phenyl)-cyclohexylamine,
(trans)-2-(2,5-dimethyl-phenyl)-cyclohexylamine,
(cis/trans)-2-(2-fluoro-phenyl)-cyclohexylamine,
(trans)-2-(2-fluoro-phenyl)-cyclohexylamine,
(cis)-2-(3-chloro-phenyl)-cyclohexylamine,
(trans)-2-(3-chloro-phenyl)-cyclohexylamine,
(cis)-2-(2,5-dichloro-phenyl)-cycloheptylamine,
(trans)-2-(2,5-dichloro-phenyl)-cycloheptylamine,
(cis)-2-(2,5-dichloro-phenyl)-cyclopentylamine,
(trans)-2-(3-methyl-pyrrol-1-yl)-cyclohexylamine,
(trans)-2-(3-ethyl-pyrrol-1-yl)-cyclohexylamine,
(trans)-2-(1,1-dioxo-[1,2]thiazinan-2-yl)-cyclohexylamine,
(trans)-1-(2-amino-cyclohexyl)-5,6-dihydro-1H-pyridin-2-one,
(trans)-1-(2-amino-cyclohexyl)-4-methyl-1,5-dihydropyrrol-2-one, (trans)-1-(2-amino-cyclohexyl)-4-methyl-5,6-dihydro-1H-pyridin-2-one, (trans)-1-(2-amino-cyclohexyl)-piperidin-2-one, (trans)-1-(2-amino-cyclohexyl)-4-methyl-pyrrolidin-2-one, and pharmaceutically acceptable salts thereof.

7. A process for manufacturing a compound according to claim 1, comprising the steps of:

a) a reductive amination of a ketone of formula II

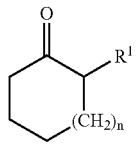

II wherein $R^1$ and n are as defined in claim 1, or b) a deprotection of a carbamic acid ester of formula III

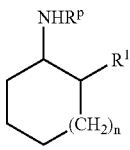

III wherein $R^1$ and n are as defined in claim 1 and $R^p$ is an amino protecting group.

8. A pharmaceutical composition, comprising a therapeutically effective amount of a compound of formula I

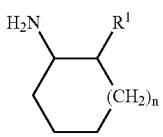

I wherein $R^1$ is selected from

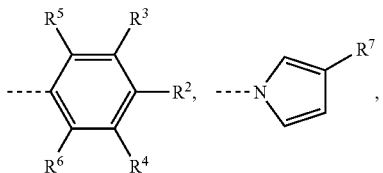

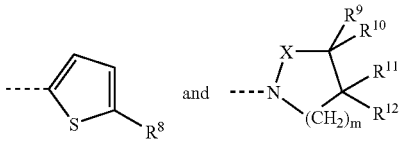

$R^2$, $R^3$, $R^4$, $R^5$ and $R^6$ are each independently selected from hydrogen, lower alkyl, halogenated lower alkyl, lower alkoxy or halogen; provided that $R^2$, $R^3$, $R^4$, $R^5$ and $R^6$ are not all hydrogen;

$R^7$ is lower alkyl;

$R^8$ is lower alkyl;

X is >C=O or >SO$_2$;

$R^9$ and $R^{11}$ are hydrogen or together form a double bond;

$R^{10}$ and $R^{12}$ are independently selected from hydrogen or lower alkyl;

m is 1 or 2; and n is 0, 1, or 2;

or a pharmaceutically acceptable salt thereof;

and a pharmaceutically acceptable carrier and/or adjuvant.

9. A pharmaceutical composition, comprising a therapeutically effective amount of a compound according to claim 1 and a pharmaceutically acceptable carrier and/or adjuvant.

10. A method for the treatment of diseases which are associated with DPP-IV, comprising the step of administering a compound according to claim 1 to a human being or animal in need thereof.

11. The method according to claim 10, wherein said disease is non-insulin dependent diabetes mellitus, impaired glucose tolerance, obesity, metabolic syndrome or β-cell protection.

* * * * *